(12) United States Patent
Medvedev et al.

(10) Patent No.: US 11,639,722 B2
(45) Date of Patent: *May 2, 2023

(54) PRESSURE/FLOW CHARACTERISTIC MODIFICATION OF A CENTRIFUGAL PUMP IN A VENTRICULAR ASSIST DEVICE

(71) Applicant: TC1 LLC, Pleasanton, CA (US)

(72) Inventors: Alexander Medvedev, Ann Arbor, MI (US); Muhammad Sami, Ypsilanti, MI (US)

(73) Assignee: TC1 LLC, St. Paul, MN (US)

( * ) Notice: Subject to any disclaimer, the term of this patent is extended or adjusted under 35 U.S.C. 154(b) by 21 days.

This patent is subject to a terminal disclaimer.

(21) Appl. No.: 17/135,425

(22) Filed: Dec. 28, 2020

(65) Prior Publication Data

US 2021/0113828 A1 Apr. 22, 2021

Related U.S. Application Data

(63) Continuation of application No. 16/173,589, filed on Oct. 29, 2018, now Pat. No. 10,888,645, which is a
(Continued)

(51) Int. Cl.
*A61M 60/00* (2021.01)
*F04D 15/00* (2006.01)
(Continued)

(52) U.S. Cl.
CPC ....... *F04D 15/0066* (2013.01); *A61M 60/148* (2021.01); *A61M 60/178* (2021.01);
(Continued)

(58) Field of Classification Search
CPC .............. A61M 60/232; A61M 60/546; A61M 2205/3334
See application file for complete search history.

(56) References Cited

U.S. PATENT DOCUMENTS 1,093,868 A 4/1914 Leighty
2,684,035 A 7/1954 Kemp
(Continued)

FOREIGN PATENT DOCUMENTS

CN 1347585 A 5/2002
CN 1462344 A 12/2003
(Continued)

OTHER PUBLICATIONS

European Application No. EP16867042.0 received a Decision to Grant dated Apr. 1, 2021, 2 pages.
(Continued)

*Primary Examiner* — Eric D. Bertram
(74) *Attorney, Agent, or Firm* — Kilpatrick Townsend & Stockton LLP

(57) ABSTRACT

A ventricular assist device is disclosed. The ventricular assist device may include a centrifugal pump and a controller. The controller may be configured to cause the centrifugal pump to operate at a first speed above a predetermined flow rate. The controller may also be configured to cause the centrifugal pump to operate at a second speed below the predetermined flow rate, wherein the predetermined flowrate is indicative of a crossover point between systole and diastole phases of a person's cardiac cycle.

14 Claims, 6 Drawing Sheets

Related U.S. Application Data continuation of application No. 15/352,141, filed on Nov. 15, 2016, now Pat. No. 10,117,983.

(60) Provisional application No. 62/255,774, filed on Nov. 16, 2015.

(51) Int. Cl.

| | |
|---|---|
| *F04D 13/06* | (2006.01) |
| *F04D 29/22* | (2006.01) |
| *A61M 60/148* | (2021.01) |
| *A61M 60/546* | (2021.01) |
| *A61M 60/232* | (2021.01) |
| *A61M 60/411* | (2021.01) |
| *A61M 60/178* | (2021.01) |
| *A61M 60/585* | (2021.01) |

(52) U.S. Cl.
CPC ........ *A61M 60/232* (2021.01); *A61M 60/411* (2021.01); *A61M 60/546* (2021.01); *A61M 60/585* (2021.01); *F04D 13/06* (2013.01); *F04D 15/0088* (2013.01); *F04D 29/22* (2013.01); *A61M 2205/3334* (2013.01); *F05D 2270/3061* (2013.01)

(56) References Cited

U.S. PATENT DOCUMENTS

| | | |
|---|---|---|
| 3,023,334 A | 2/1962 | Burr et al. |
| 3,152,017 A | 10/1964 | Parent et al. |
| 3,510,229 A | 5/1970 | Smith |
| 3,620,638 A | 11/1971 | Kaye et al. |
| 3,870,382 A | 3/1975 | Reinhoudt |
| 3,932,069 A | 1/1976 | Giardini et al. |
| 3,960,468 A | 6/1976 | Boorse et al. |
| 4,149,535 A | 4/1979 | Voider |
| 4,382,199 A | 5/1983 | Isaacson |
| 4,392,836 A | 7/1983 | Sugawara |
| 4,434,389 A | 2/1984 | Langley et al. |
| 4,507,048 A | 3/1985 | Belenger et al. |
| 4,528,485 A | 7/1985 | Boyd, Jr. |
| 4,540,402 A | 9/1985 | Aigner |
| 4,549,860 A | 10/1985 | Yakich |
| 4,645,961 A | 2/1987 | Maisky |
| 4,686,982 A | 8/1987 | Nash |
| 4,688,998 A | 8/1987 | Olsen et al. |
| 4,753,221 A | 6/1988 | Kensey et al. |
| 4,769,006 A | 9/1988 | Papatonakos |
| 4,779,614 A | 10/1988 | Moise |
| 4,790,843 A | 12/1988 | Carpentier et al. |
| 4,806,080 A | 2/1989 | Mizobuchi et al. |
| 4,817,586 A | 4/1989 | Wampler |
| 4,846,152 A | 7/1989 | Wampler et al. |
| 4,857,781 A | 8/1989 | Shih |
| 4,888,011 A | 12/1989 | Kung et al. |
| 4,895,557 A | 1/1990 | Moise et al. |
| 4,900,227 A | 2/1990 | Troup lin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,930,997 A | 6/1990 | Bennett |
| 4,944,722 A | 7/1990 | Carriker et al. |
| 4,957,504 A | 9/1990 | Chardack |
| 4,964,864 A | 10/1990 | Summers et al. |
| 4,969,865 A | 11/1990 | Hwang et al. |
| 4,985,014 A | 1/1991 | Orejola |
| 4,995,857 A | 2/1991 | Arnold |
| 5,021,048 A | 6/1991 | Buckholtz |
| 5,078,741 A | 1/1992 | Bramm et al. |
| 5,092,844 A | 3/1992 | Schwartz et al. |
| 5,092,879 A | 3/1992 | Jarvik |
| 5,100,374 A | 3/1992 | Kageyama |
| 5,106,263 A | 4/1992 | Irie |
| 5,106,273 A | 4/1992 | Lemarquand et al. |
| 5,106,372 A | 4/1992 | Ranford |
| 5,112,202 A | 5/1992 | Oshima et al. |
| 5,112,349 A | 5/1992 | Summers et al. |
| 5,129,883 A | 7/1992 | Black |
| 5,145,333 A | 9/1992 | Smith |
| 5,147,186 A | 9/1992 | Buckholtz |
| 5,190,528 A | 3/1993 | Fonger et al. |
| 5,201,679 A | 4/1993 | Velte et al. |
| 5,211,546 A | 5/1993 | Isaacson et al. |
| 5,229,693 A | 7/1993 | Futami et al. |
| 5,275,580 A | 1/1994 | Yamazaki |
| 5,290,227 A | 3/1994 | Pasque |
| 5,290,236 A | 3/1994 | Mathewson |
| 5,300,112 A | 4/1994 | Barr |
| 5,306,295 A | 4/1994 | Kolff et al. |
| 5,312,341 A | 5/1994 | Turi |
| 5,313,128 A | 5/1994 | Robinson et al. |
| 5,332,374 A | 7/1994 | Kricker et al. |
| 5,346,458 A | 9/1994 | Afield |
| 5,350,283 A | 9/1994 | Nakazeki et al. |
| 5,354,331 A | 10/1994 | Schachar |
| 5,360,445 A | 11/1994 | Goldowsky |
| 5,370,509 A | 12/1994 | Golding et al. |
| 5,376,114 A | 12/1994 | Jarvik |
| 5,385,581 A | 1/1995 | Bramm et al. |
| 5,405,383 A | 4/1995 | Barr |
| 5,449,342 A | 9/1995 | Hirose et al. |
| 5,478,222 A | 12/1995 | Heidelberg et al. |
| 5,504,978 A | 4/1996 | Meyer, III |
| 5,507,629 A | 4/1996 | Jarvik |
| 5,519,270 A | 5/1996 | Yamada et al. |
| 5,533,957 A | 7/1996 | Aldea |
| 5,569,111 A | 10/1996 | Cho et al. |
| 5,575,630 A | 11/1996 | Nakazawa et al. |
| 5,588,812 A | 12/1996 | Taylor et al. |
| 5,595,762 A | 1/1997 | Derrieu et al. |
| 5,611,679 A | 3/1997 | Ghosh et al. |
| 5,613,935 A | 3/1997 | Jarvik |
| 5,630,836 A | 5/1997 | Prem et al. |
| 5,643,226 A | 7/1997 | Cosgrove et al. |
| 5,678,306 A | 10/1997 | Bozeman, Jr. et al. |
| 5,692,882 A | 12/1997 | Bozeman, Jr. et al. |
| 5,695,471 A | 12/1997 | Wampler |
| 5,708,346 A | 1/1998 | Schob |
| 5,725,357 A | 3/1998 | Nakazeki et al. |
| 5,738,649 A | 4/1998 | Macoviak |
| 5,746,575 A | 5/1998 | Westphal et al. |
| 5,746,709 A | 5/1998 | Rom et al. |
| 5,749,855 A | 5/1998 | Reitan |
| 5,755,784 A | 5/1998 | Jarvik |
| 5,776,111 A | 7/1998 | Tesio |
| 5,795,074 A | 8/1998 | Rahman et al. |
| 5,800,559 A | 9/1998 | Higham et al. |
| 5,807,311 A | 9/1998 | Palestrant |
| 5,814,011 A | 9/1998 | Corace |
| 5,824,069 A | 10/1998 | Lemole |
| 5,843,129 A | 12/1998 | Larson et al. |
| 5,851,174 A | 12/1998 | Jarvik et al. |
| 5,853,394 A | 12/1998 | Tolkoff et al. |
| 5,868,702 A | 2/1999 | Stevens et al. |
| 5,868,703 A | 2/1999 | Bertolero et al. |
| 5,888,242 A * | 3/1999 | Antaki ............... A61M 60/178 623/3.28 |
| 5,890,883 A | 4/1999 | Golding et al. |
| 5,911,685 A | 6/1999 | Siess et al. |
| 5,917,295 A | 6/1999 | Mongeau |
| 5,917,297 A | 6/1999 | Gerster et al. |
| 5,921,913 A | 7/1999 | Siess |
| 5,924,848 A | 7/1999 | Izraelev |
| 5,924,975 A | 7/1999 | Goldowsky |
| 5,928,131 A | 7/1999 | Prem |
| 5,938,412 A | 8/1999 | Israelev |
| 5,941,813 A | 8/1999 | Sievers et al. |
| 5,945,753 A | 8/1999 | Maegawa et al. |
| 5,947,703 A | 9/1999 | Nojiri et al. |
| 5,951,263 A | 9/1999 | Taylor et al. |
| 5,964,694 A | 10/1999 | Siess et al. |
| 5,984,892 A | 11/1999 | Bedingham |

(56) References Cited

U.S. PATENT DOCUMENTS

| | | |
|---|---|---|
| 6,004,269 A | 12/1999 | Crowley et al. |
| 6,007,479 A | 12/1999 | Rottenberg et al. |
| 6,030,188 A | 2/2000 | Nojiri et al. |
| 6,042,347 A | 3/2000 | Scholl et al. |
| 6,053,705 A | 4/2000 | Schob et al. |
| 6,058,593 A | 5/2000 | Siess |
| 6,066,086 A * | 5/2000 | Antaki ............... A61M 60/546 600/17 |
| 6,071,093 A | 6/2000 | Hart |
| 6,074,180 A | 6/2000 | Khanwilkar et al. |
| 6,080,133 A | 6/2000 | Wampler |
| 6,082,900 A | 7/2000 | Takeuchi et al. |
| 6,083,260 A | 7/2000 | Aboul-Hosn et al. |
| 6,086,527 A | 7/2000 | Talpade |
| 6,100,618 A | 8/2000 | Schoeb et al. |
| 6,123,659 A | 9/2000 | leBlanc et al. |
| 6,123,726 A | 9/2000 | Mori et al. |
| 6,139,487 A | 10/2000 | Siess |
| 6,142,752 A | 11/2000 | Akamatsu et al. |
| 6,143,025 A | 11/2000 | Stobie et al. |
| 6,146,325 A | 11/2000 | Lewis et al. |
| 6,149,683 A | 11/2000 | Lancisi et al. |
| 6,158,984 A | 12/2000 | Cao et al. |
| 6,171,078 B1 | 1/2001 | Schob |
| 6,176,822 B1 | 1/2001 | Nix et al. |
| 6,176,848 B1 | 1/2001 | Rau et al. |
| 6,179,773 B1 | 1/2001 | Prem et al. |
| 6,190,304 B1 | 2/2001 | Downey et al. |
| 6,200,260 B1 | 3/2001 | Bolling |
| 6,206,659 B1 | 3/2001 | Izraelev |
| 6,222,290 B1 | 4/2001 | Schob et al. |
| 6,227,797 B1 | 5/2001 | Watterson et al. |
| 6,227,820 B1 | 5/2001 | Jarvik |
| 6,234,772 B1 | 5/2001 | Wampler et al. |
| 6,234,998 B1 | 5/2001 | Wampler |
| 6,245,007 B1 | 6/2001 | Bedingham et al. |
| 6,247,892 B1 | 6/2001 | Kazatchkov et al. |
| 6,249,067 B1 | 6/2001 | Schob et al. |
| 6,254,359 B1 | 7/2001 | Aber |
| 6,264,635 B1 | 7/2001 | Wampler et al. |
| 6,268,675 B1 | 7/2001 | Amrhein |
| 6,276,831 B1 | 8/2001 | Takahashi et al. |
| 6,293,901 B1 | 9/2001 | Prem |
| 6,295,877 B1 | 10/2001 | Aboul-Hosn et al. |
| 6,319,231 B1 | 11/2001 | Andrulitis |
| 6,320,731 B1 | 11/2001 | Eeaves et al. |
| 6,351,048 B1 | 2/2002 | Schob et al. |
| 6,355,998 B1 | 3/2002 | Schob et al. |
| 6,365,996 B2 | 4/2002 | Schob |
| 6,375,607 B1 | 4/2002 | Prem |
| 6,387,037 B1 | 5/2002 | Bolling et al. |
| 6,394,769 B1 | 5/2002 | Bearnson et al. |
| 6,422,990 B1 | 7/2002 | Prem |
| 6,425,007 B1 | 7/2002 | Messinger |
| 6,428,464 B1 | 8/2002 | Bolling |
| 6,439,845 B1 | 8/2002 | Veres |
| 6,447,266 B2 | 9/2002 | Antaki et al. |
| 6,447,441 B1 | 9/2002 | Yu et al. |
| 6,458,163 B1 | 10/2002 | Slemker et al. |
| 6,508,777 B1 | 1/2003 | Macoviak et al. |
| 6,508,787 B2 | 1/2003 | Erbel et al. |
| 6,517,315 B2 | 2/2003 | Belady |
| 6,522,093 B1 | 2/2003 | Hsu et al. |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | deBlanc et al. |
| 6,547,530 B2 | 4/2003 | Ozaki et al. |
| 6,575,717 B2 | 6/2003 | Ozaki et al. |
| 6,589,030 B2 | 7/2003 | Ozaki |
| 6,595,762 B2 | 7/2003 | Khanwilkar et al. |
| 6,605,032 B2 | 8/2003 | Benkowski et al. |
| 6,609,883 B2 | 8/2003 | Woodard et al. |
| 6,610,004 B2 | 8/2003 | Viole et al. |
| 6,623,420 B2 | 9/2003 | Reich et al. |
| 6,641,378 B2 | 11/2003 | Davis et al. |
| 6,641,558 B1 | 11/2003 | Aboul-Hosn et al. |
| 6,688,861 B2 | 2/2004 | Wampler |
| 6,692,318 B2 | 2/2004 | McBride |
| 6,698,097 B1 | 3/2004 | Miura et al. |
| 6,709,418 B1 | 3/2004 | Aboul-Hosn et al. |
| 6,716,157 B2 | 4/2004 | Goldowsky |
| 6,716,189 B1 | 4/2004 | Jarvik et al. |
| 6,732,501 B2 | 5/2004 | Yu et al. |
| 6,749,598 B1 | 6/2004 | Keren et al. |
| 6,776,578 B2 | 8/2004 | Belady |
| 6,790,171 B1 | 9/2004 | Griindeman et al. |
| 6,794,789 B2 | 9/2004 | Siess et al. |
| 6,808,371 B2 | 10/2004 | Niwatsukino et al. |
| 6,817,836 B2 | 11/2004 | Nose et al. |
| 6,846,168 B2 | 1/2005 | Davis et al. |
| 6,860,713 B2 | 3/2005 | Hoover |
| 6,884,210 B2 | 4/2005 | Nose et al. |
| 6,926,662 B1 | 8/2005 | Aboul-Hosn et al. |
| 6,935,344 B1 | 8/2005 | Aboul-Hosn et al. |
| 6,942,672 B2 | 9/2005 | Heilman et al. |
| 6,949,066 B2 | 9/2005 | Beamson et al. |
| 6,966,748 B2 | 11/2005 | Woodard et al. |
| 6,974,436 B1 | 12/2005 | Aboul-Hosn et al. |
| 6,991,595 B2 | 1/2006 | Burke et al. |
| 7,010,954 B2 | 3/2006 | Siess et al. |
| 7,011,620 B1 | 3/2006 | Siess |
| 7,022,100 B1 | 4/2006 | Aboul-Hosn et al. |
| 7,027,875 B2 | 4/2006 | Siess et al. |
| 7,048,681 B2 | 5/2006 | Tsubouchi et al. |
| 7,089,059 B1 | 8/2006 | Pless |
| 7,090,401 B2 | 8/2006 | Rahman et al. |
| 7,112,903 B1 | 9/2006 | Schob |
| 7,122,019 B1 | 10/2006 | Kesten et al. |
| 7,128,538 B2 | 10/2006 | Tsubouchi et al. |
| 7,156,802 B2 | 1/2007 | Woodard et al. |
| 7,160,243 B2 | 1/2007 | Medvedev |
| 7,172,551 B2 | 2/2007 | Leasure |
| 7,175,588 B2 | 2/2007 | Morello |
| 7,202,582 B2 | 4/2007 | Eckert et al. |
| 7,241,257 B1 | 7/2007 | Ainsworth et al. |
| 7,284,956 B2 | 10/2007 | Nose et al. |
| 7,329,236 B2 | 2/2008 | Kesten et al. |
| 7,331,921 B2 | 2/2008 | Viole et al. |
| 7,335,192 B2 | 2/2008 | Keren et al. |
| 7,393,181 B2 | 7/2008 | McBride et al. |
| 7,431,688 B2 | 10/2008 | Wampler et al. |
| 7,462,019 B1 | 12/2008 | Allarie et al. |
| 7,467,930 B2 | 12/2008 | Ozaki et al. |
| 7,470,246 B2 | 12/2008 | Mori et al. |
| 7,476,077 B2 | 1/2009 | Woodard et al. |
| 7,491,163 B2 | 2/2009 | Viole et al. |
| 7,575,423 B2 | 8/2009 | Wampler |
| 7,645,225 B2 | 1/2010 | Medvedev et al. |
| 7,660,635 B1 | 2/2010 | Verness et al. |
| 7,699,586 B2 | 4/2010 | LaRose et al. |
| 7,731,675 B2 | 6/2010 | Aboul-Hosn et al. |
| 7,748,964 B2 | 7/2010 | Yaegashi et al. |
| 7,802,966 B2 | 9/2010 | Wampler et al. |
| 7,841,976 B2 | 11/2010 | McBride et al. |
| 7,862,501 B2 | 1/2011 | Woodard |
| 7,888,242 B2 | 2/2011 | Tanaka et al. |
| 7,934,909 B2 | 5/2011 | Nuesser et al. |
| 7,972,122 B2 | 7/2011 | LaRose et al. |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,096,935 B2 | 1/2012 | Sutton et al. |
| 8,123,669 B2 | 2/2012 | Siess et al. |
| 8,152,493 B2 | 4/2012 | LaRose et al. |
| 8,177,703 B2 | 5/2012 | Smith et al. |
| 8,226,373 B2 | 7/2012 | Yaehashi |
| 8,282,359 B2 | 10/2012 | Ayre et al. |
| 8,283,829 B2 | 10/2012 | Yamamoto et al. |
| 8,366,381 B2 | 2/2013 | Woodard et al. |
| 8,403,823 B2 | 3/2013 | Yu et al. |
| 8,512,012 B2 | 8/2013 | Mustafa et al. |
| 8,535,211 B2 | 9/2013 | Campbell et al. |
| 8,585,290 B2 | 11/2013 | Bauer |

(56) References Cited

U.S. PATENT DOCUMENTS

| | | | |
|---|---|---|---|
| 8,686,674 B2 | 4/2014 | Bi et al. | |
| 8,770,945 B2 | 7/2014 | Ozaki et al. | |
| 8,821,365 B2 | 9/2014 | Ozaki et al. | |
| 8,827,661 B2 | 9/2014 | Mori | |
| 8,652,024 B1 | 10/2014 | Yanai et al. | |
| 8,864,644 B2 | 10/2014 | Yomtov | |
| 8,870,552 B2 | 10/2014 | Ayre et al. | |
| 8,968,174 B2 | 3/2015 | Yanai et al. | |
| 9,039,595 B2 | 5/2015 | Ayre et al. | |
| 9,067,005 B2 | 6/2015 | Ozaki et al. | |
| 9,068,572 B2 | 6/2015 | Ozaki et al. | |
| 9,109,601 B2 | 8/2015 | Mori | |
| 9,132,215 B2 | 9/2015 | Ozaki et al. | |
| 9,133,854 B2 | 9/2015 | Okawa et al. | |
| 9,371,826 B2 | 6/2016 | Yanai et al. | |
| 9,381,285 B2 | 7/2016 | Ozaki et al. | |
| 9,382,908 B2 | 7/2016 | Ozaki et al. | |
| 9,410,549 B2 | 8/2016 | Ozaki et al. | |
| 9,556,873 B2 | 1/2017 | Yanai et al. | |
| 9,713,663 B2 | 7/2017 | Medvedev et al. | |
| 10,117,983 B2 * | 11/2018 | Medvedev | F04D 15/0066 |
| 10,888,645 B2 * | 1/2021 | Medvedev | A61M 60/546 |
| 2001/0039369 A1 | 11/2001 | Terentiev | |
| 2002/0051711 A1 | 5/2002 | Ozaki | |
| 2002/0058994 A1 | 5/2002 | Hill et al. | |
| 2002/0094281 A1 | 7/2002 | Khanwilkar et al. | |
| 2002/0095210 A1 | 7/2002 | Finnegan et al. | |
| 2003/0023302 A1 | 1/2003 | Moe et al. | |
| 2003/0045772 A1 | 3/2003 | Reich et al. | |
| 2003/0072656 A1 | 4/2003 | Niwatsukino et al. | |
| 2003/0144574 A1 | 7/2003 | Heilman et al. | |
| 2003/0199727 A1 | 10/2003 | Burke | |
| 2003/0236488 A1 | 12/2003 | Novak | |
| 2003/0236490 A1 | 12/2003 | Novak | |
| 2004/0007515 A1 | 1/2004 | Geyer | |
| 2004/0015232 A1 | 1/2004 | Shu et al. | |
| 2004/0024285 A1 | 2/2004 | Muckter | |
| 2004/0030381 A1 | 2/2004 | Shu | |
| 2004/0064012 A1 * | 4/2004 | Yanai | A61M 60/546 |
| | | | 600/16 |
| 2004/0143151 A1 | 7/2004 | Mori et al. | |
| 2004/0145337 A1 | 7/2004 | Morishita | |
| 2004/0152944 A1 | 8/2004 | Medvedev et al. | |
| 2004/0171905 A1 | 9/2004 | Yu et al. | |
| 2004/0210305 A1 | 10/2004 | Shu et al. | |
| 2004/0215050 A1 | 10/2004 | Morello | |
| 2004/0263341 A1 | 12/2004 | Enzinna | |
| 2005/0004418 A1 | 1/2005 | Morello | |
| 2005/0008496 A1 | 1/2005 | Tsubouchi et al. | |
| 2005/0025630 A1 | 2/2005 | Ayre et al. | |
| 2005/0043665 A1 | 2/2005 | Vinci et al. | |
| 2005/0073273 A1 | 4/2005 | Maslov et al. | |
| 2005/0089422 A1 | 4/2005 | Ozaki et al. | |
| 2005/0131271 A1 | 6/2005 | Benkowski et al. | |
| 2005/0141887 A1 | 6/2005 | Lelkes | |
| 2005/0194851 A1 | 9/2005 | Eckert et al. | |
| 2005/0261542 A1 | 11/2005 | Abe et al. | |
| 2005/0287022 A1 | 12/2005 | Yaegashi et al. | |
| 2006/0024182 A1 | 2/2006 | Akdis et al. | |
| 2006/0055274 A1 | 3/2006 | Kim | |
| 2006/0127227 A1 | 6/2006 | Mehlhorn et al. | |
| 2007/0073393 A1 | 3/2007 | Kung et al. | |
| 2007/0078293 A1 | 4/2007 | Shambaugh, Jr. | |
| 2007/0095648 A1 | 4/2007 | Wampler et al. | |
| 2007/0114961 A1 | 5/2007 | Schwarzkopf | |
| 2007/0134993 A1 | 6/2007 | Tamez et al. | |
| 2007/0189648 A1 | 8/2007 | Kita et al. | |
| 2007/0213690 A1 | 9/2007 | Phillips et al. | |
| 2007/0231135 A1 | 10/2007 | Wampler et al. | |
| 2007/0282298 A1 | 12/2007 | Mason | |
| 2007/0297923 A1 | 12/2007 | Tada | |
| 2008/0007196 A1 | 1/2008 | Tan et al. | |
| 2008/0021394 A1 | 1/2008 | La Rose et al. | |
| 2008/0030895 A1 | 2/2008 | Obara et al. | |
| 2008/0119777 A1 | 5/2008 | Vinci et al. | |
| 2008/0124231 A1 | 5/2008 | Yaegashi | |
| 2008/0183287 A1 | 7/2008 | Ayre | |
| 2008/0211439 A1 | 9/2008 | Yokota et al. | |
| 2008/0281146 A1 | 11/2008 | Morello | |
| 2009/0041595 A1 | 2/2009 | Garzaniti et al. | |
| 2009/0060743 A1 | 3/2009 | McBride et al. | |
| 2009/0074336 A1 | 3/2009 | Engesser et al. | |
| 2009/0099406 A1 | 4/2009 | Salmonsen et al. | |
| 2009/0171136 A1 | 7/2009 | Shambaugh, Jr. | |
| 2009/0257693 A1 | 10/2009 | Aiello | |
| 2009/0318834 A1 | 12/2009 | Fujiwara et al. | |
| 2010/0185280 A1 | 6/2010 | Ayre et al. | |
| 2010/0168534 A1 | 7/2010 | Matsumoto et al. | |
| 2010/0222634 A1 | 9/2010 | Poirier | |
| 2010/0234835 A1 | 9/2010 | Horikawa et al. | |
| 2010/0256440 A1 | 10/2010 | Maher | |
| 2010/0262039 A1 | 10/2010 | Fujiwara et al. | |
| 2010/0266423 A1 | 10/2010 | Gohean et al. | |
| 2010/0305692 A1 | 12/2010 | Thomas et al. | |
| 2010/0324465 A1 | 12/2010 | Vinci et al. | |
| 2011/0015732 A1 | 1/2011 | Kanebako | |
| 2011/0054239 A1 | 3/2011 | Sutton et al. | |
| 2011/0112354 A1 | 5/2011 | Nishimura et al. | |
| 2011/0118766 A1 | 5/2011 | Reichenbach et al. | |
| 2011/0118829 A1 | 5/2011 | Hoarau et al. | |
| 2011/0118833 A1 | 5/2011 | Reichenbach et al. | |
| 2011/0129373 A1 | 6/2011 | Mori | |
| 2011/0160519 A1 | 6/2011 | Arndt et al. | |
| 2011/0218383 A1 | 9/2011 | Broen et al. | |
| 2011/0218384 A1 | 9/2011 | Bachman et al. | |
| 2011/0218385 A1 | 9/2011 | Bolyare et al. | |
| 2011/0237978 A1 | 9/2011 | Fujiwara et al. | |
| 2011/0243759 A1 | 10/2011 | Ozaki et al. | |
| 2011/0318203 A1 | 12/2011 | Ozaki et al. | |
| 2012/0003108 A1 | 1/2012 | Ozaki et al. | |
| 2012/0016178 A1 | 1/2012 | Woodard et al. | |
| 2012/0022645 A1 | 1/2012 | Burke | |
| 2012/0035411 A1 | 2/2012 | LaRose et al. | |
| 2012/0078030 A1 | 3/2012 | Bourque | |
| 2012/0078031 A1 | 3/2012 | Burke et al. | |
| 2012/0095281 A1 | 4/2012 | Reichenbach et al. | |
| 2012/0130152 A1 | 5/2012 | Ozaki et al. | |
| 2012/0226350 A1 | 9/2012 | Ruder et al. | |
| 2012/0243759 A1 | 9/2012 | Fujisawa | |
| 2012/0245681 A1 | 9/2012 | Casas et al. | |
| 2012/0253103 A1 | 10/2012 | Jarvik | |
| 2012/0308363 A1 | 12/2012 | Ozaki et al. | |
| 2013/0030240 A1 | 1/2013 | Schima et al. | |
| 2013/0121821 A1 | 5/2013 | Ozaki et al. | |
| 2013/0158521 A1 | 6/2013 | Sobue | |
| 2013/0170970 A1 | 7/2013 | Ozaki et al. | |
| 2013/0178694 A1 | 7/2013 | Jeffery et al. | |
| 2013/0225909 A1 | 8/2013 | Dormanen et al. | |
| 2013/0243623 A1 | 9/2013 | Okawa et al. | |
| 2013/0289334 A1 | 10/2013 | Badstibner et al. | |
| 2013/0331711 A1 | 12/2013 | Mathur et al. | |
| 2014/0030122 A1 | 1/2014 | Ozaki et al. | |
| 2014/0066690 A1 | 3/2014 | Siebenhaar et al. | |
| 2014/0066691 A1 | 3/2014 | Siebenhaar | |
| 2014/0100413 A1 | 4/2014 | Casas et al. | |
| 2014/0107399 A1 | 4/2014 | Spence | |
| 2014/0142367 A1 | 5/2014 | Ayre et al. | |
| 2014/0155682 A1 | 6/2014 | Jeffery et al. | |
| 2014/0200389 A1 | 7/2014 | Yanai et al. | |
| 2014/0205467 A1 | 7/2014 | Yanai et al. | |
| 2014/0241904 A1 | 8/2014 | Yanai et al. | |
| 2014/0275721 A1 | 9/2014 | Yanai et al. | |
| 2014/0275727 A1 | 9/2014 | Bonde et al. | |
| 2014/0296615 A1 | 10/2014 | Franano | |
| 2014/0309481 A1 | 10/2014 | Medvedev et al. | |
| 2014/0314597 A1 | 10/2014 | Allaire et al. | |
| 2014/0323796 A1 * | 10/2014 | Medvedev | A61M 60/232 |
| | | | 600/17 |
| 2014/0343352 A1 | 11/2014 | Ardt et al. | |
| 2015/0017030 A1 | 1/2015 | Ozaki | |
| 2015/0023803 A1 | 1/2015 | Fritz et al. | |
| 2015/0078936 A1 | 3/2015 | Mori | |
| 2015/0306290 A1 | 10/2015 | Rosenberg et al. | |
| 2015/0367048 A1 | 12/2015 | Brown et al. | |

(56) References Cited

U.S. PATENT DOCUMENTS

| | | |
|---|---|---|
| 2015/0374892 A1 | 12/2015 | Yanai et al. |
| 2016/0058929 A1 | 3/2016 | Medvedev et al. |
| 2016/0058930 A1 | 3/2016 | Medvedev et al. |
| 2016/0228628 A1 | 8/2016 | Medvedev et al. |
| 2016/0235898 A1 | 8/2016 | Yanai et al. |
| 2016/0235899 A1 | 8/2016 | Yu et al. |
| 2016/0235900 A1 | 8/2016 | Yanai et al. |
| 2016/0281720 A1 | 9/2016 | Yanai et al. |
| 2016/0281728 A1 | 9/2016 | Ozaki et al. |

FOREIGN PATENT DOCUMENTS

| | | |
|---|---|---|
| CN | 102239334 A | 11/2011 |
| CN | 102341600 A | 2/2012 |
| EP | 2945662 B1 | 9/1999 |
| EP | 971212 A | 1/2000 |
| EP | 1113117 A2 | 7/2001 |
| EP | 1327455 A | 7/2003 |
| EP | 1430919 A1 | 6/2004 |
| EP | 1495773 A2 | 1/2005 |
| EP | 1526286 A2 | 4/2005 |
| EP | 1598087 A2 | 11/2005 |
| EP | 1495773 A3 | 11/2006 |
| EP | 1495773 B1 | 2/2009 |
| EP | 2292282 A1 | 3/2011 |
| EP | 2298375 A1 | 3/2011 |
| EP | 2372160 A1 | 10/2011 |
| EP | 2405140 A1 | 1/2012 |
| EP | 2405141 A1 | 1/2012 |
| EP | 2461465 A1 | 6/2012 |
| EP | 2538086 A1 | 12/2012 |
| EP | 2554191 A1 | 2/2013 |
| EP | 2594799 A1 | 5/2013 |
| EP | 2618001 A1 | 7/2013 |
| EP | 2693609 A1 | 2/2014 |
| EP | 2948202 A1 | 12/2015 |
| EP | 2961987 A1 | 1/2016 |
| EP | 3013385 A2 | 5/2016 |
| JP | 589535 | 1/1983 |
| JP | 61-293146 | 12/1986 |
| JP | H02-007780 U | 1/1990 |
| JP | H02-033590 U | 3/1990 |
| JP | 04-091396 A | 3/1992 |
| JP | 04-148094 A | 5/1992 |
| JP | 05-021197 U | 3/1993 |
| JP | 06-014538 U | 2/1994 |
| JP | 06-053790 U | 7/1994 |
| JP | 2006-070476 | 9/1994 |
| JP | 2006-245455 | 9/1994 |
| JP | 07-014220 U | 3/1995 |
| JP | 07-042869 U | 8/1995 |
| JP | 07-509156 A | 10/1995 |
| JP | 09-122228 A | 5/1997 |
| JP | 10-331841 A | 12/1998 |
| JP | 11-244377 A | 9/1999 |
| JP | 2001-309628 | 11/2001 |
| JP | 2003-135592 A | 5/2003 |
| JP | 2004-166401 A | 6/2004 |
| JP | 2004-209240 A | 7/2004 |
| JP | 2004-332566 A | 11/2004 |
| JP | 2004-346925 A | 12/2004 |
| JP | 2005-094955 | 4/2005 |
| JP | 2005-127222 A | 5/2005 |
| JP | 2005-245138 | 9/2005 |
| JP | 2005-270345 A | 10/2005 |
| JP | 2005-270415 A | 10/2005 |
| JP | 2005-287599 A | 10/2005 |
| JP | 2006-167173 A | 6/2006 |
| JP | 2007-002885 A | 1/2007 |
| JP | 2007-043821 | 2/2007 |
| JP | 2007-089972 A | 4/2007 |
| JP | 2007-089974 | 4/2007 |
| JP | 2007-215292 | 8/2007 |
| JP | 2007-247489 | 9/2007 |
| JP | 2008-011611 | 1/2008 |
| JP | 2008-104278 | 5/2008 |
| JP | 2008-132131 | 6/2008 |
| JP | 2008-99453 | 8/2008 |
| JP | 2008-193838 | 8/2008 |
| JP | 2008-297997 A | 12/2008 |
| JP | 2008-301634 | 12/2008 |
| JP | 2006-254619 | 9/2009 |
| JP | 2010-133381 A | 6/2010 |
| JP | 2010-136863 A | 6/2010 |
| JP | 2010-203398 A | 9/2010 |
| JP | 2010-209691 A | 9/2010 |
| JP | 2011-169166 A | 9/2011 |
| JP | 2012-021413 | 2/2012 |
| JP | 2012-062790 A | 3/2012 |
| JP | 5171953 B2 | 3/2013 |
| JP | 5572832 B2 | 8/2014 |
| JP | 5656835 B2 | 1/2015 |
| WO | 1993-07388 A1 | 4/1993 |
| WO | 94-14226 | 6/1994 |
| WO | 1996-31934 | 10/1996 |
| WO | 1997-42413 A1 | 11/1997 |
| WO | 2000-64509 A1 | 11/2000 |
| WO | 2004-098677 A1 | 11/2004 |
| WO | 2005-011087 A1 | 2/2005 |
| WO | 2005-028000 A1 | 3/2005 |
| WO | 2005-034312 A2 | 4/2005 |
| WO | 2009-157408 A1 | 12/2009 |
| WO | 2010-067682 A1 | 6/2010 |
| WO | 2010-101082 A1 | 9/2010 |
| WO | 2010-101107 A1 | 9/2010 |
| WO | 2011-013483 A1 | 2/2011 |
| WO | 2012-036059 A1 | 3/2012 |
| WO | 2012-040544 A1 | 3/2012 |
| WO | 2012-047550 A1 | 4/2012 |
| WO | 2012-132850 A1 | 10/2012 |
| WO | 2014-113533 A1 | 7/2014 |
| WO | 2014-116676 A1 | 7/2014 |
| WO | 2014-133942 A1 | 9/2014 |
| WO | 2014-179271 A2 | 11/2014 |
| WO | 2016-033131 A1 | 3/2016 |
| WO | 2016-033133 A1 | 3/2016 |
| WO | 2016-130846 A1 | 8/2016 |
| WO | 2016-130944 A1 | 8/2016 |
| WO | 2016-130955 A1 | 8/2016 |
| WO | 2016-130989 A1 | 8/2016 |

OTHER PUBLICATIONS

International Application No. PCT/US2014/017932 received an International Preliminary Report on Patentability, dated Sep. 11, 2015, 7 pages.
International Application No. PCT/US2015/046846 received an International Search Report and Written Opinion, dated Oct. 27, 2015, 8 pages.
International Search Report and Written Opinion dated Feb. 24, 2017 for International Patent Application No. PCT/US2016/062284, 8 pages.
International Preliminary Report dated May 22, 2018 for International Patent Application No. PCT/US2016/062284, 6 pages.
Asama, J., et al., "A Compact Highly Efficient and Low Hemolytic Centrifugal Blood Pump With a Magnetically Levitated Impeller", Artificial Organs, vol. 30, No. 3, Mar. 1, 2006 (Mar. 1, 2006), pp. 160-167.
Asama, J., et al., "A New Design for a Compact Centrifugal Blood Pump with a Magnetically Levitated Rotor", Asaio Jopurnal, vol. 50, No. 6, Nov. 1, 2004 (Nov. 1, 2004), pp. 550-556.
Asama, et al., "Suspension Performance of a Two-Axis Actively Regulated Consequent-Pole Bearingless Motor," IEEE Transactions On Energy Conversion, vol. 28, No. 4, Dec. 2013, 8 pages.
European Search report Issued in European Patent Application No. 10748702.7, dated Apr. 2, 2013.
Extended European Search Report issued in European Patent Application No. EP 10748677.1, dated Nov. 19, 2012.
Extended European Search Report dated Apr. 2, 2015 in European Patent Application No. EP 09770118.9, filed Jun. 22, 2009, all pages.

(56) References Cited

OTHER PUBLICATIONS

European office action dated Jul. 22, 2016 for European Patent Application No. EP 09770118.9, all pages.
European office action dated Jan. 27, 2016 for EP 10804230.0, all pages.
European office action dated Oct. 31, 2016 for EP 10804230.0, all pages.
European office action dated Sep. 8, 2016 for EP 14741174, all pages.
Extended European Search Report issued in European Patent Application No. EP 11806627.3, dated Oct. 8, 2014, all pages.
Extended European Search Report issued in European Patent Application No. EP 11825062, dated Jun. 18, 2015, all pages.
European Office Action issued in Application No. EP 11825062 dated Jul. 19, 2016, all pages.
Extended European Search Report dated Feb. 4, 2016 in European Patent Application No. EP 12764433.4, filed Mar. 12, 2012, all pages.
Extended European Search Report for EP 14743371.8 dated Sep. 29, 2016, all pages.
Gieras, et al., "Advancements in Electric Machines", Nov. 14, 2008, pp. 43-48.
International Search Report (PCT/ISA/210) dated Jul. 14, 2009, by Japanese Patent Office as the International Searching Authority for International Application No. PCT/JP2009/061318, all pages.
International Search Report and Written Opinion issued in PCT/JP2011/050925, dated Apr. 12, 2011, all pages.
International Search Report and Written Opinion issued in PCT/JP2011/054134, dated Apr. 12, 2011, all pages.
International Search Report and Written Opinion issued in PCT/JP2011/064768, dated Sep. 13, 2011, all pages.
International Search Report and Written Opinion issued in PCT/JP2011/070450, dated Dec. 13, 2011, all pages.
International Search Report and Written Opinion of PCT/US2014/012448 dated Feb. 19, 2014, all pages.
International Search Report and Written Opinion of PCT/US2014/011786, dated May 5, 2014, all pages.
International Preliminary Report on Patentability dated Jul. 30, 2015 for International Patent Application No. PCT/US2014/011786, filed on Jan. 16, 2014, all pages.
International Search Report and Written Opinion of PCT/US2014/012511, dated May 14, 2014, all pages.
International Preliminary Report on Patentability dated Aug. 6, 2015 for International Patent Application No. PCT/US2014/012511, filed on Jan. 22, 2014, all pages.
International Search Report and Written Opinion of PCT/US2014/012502, dated May 9, 2014, all pages.
International Search Report and Written Opinion of PCT/US2014/017932, dated Jun. 16, 2014, all pages.
International Preliminary Report on Patentability dated Aug. 6, 2015 for International Patent Application No. PCT/US2014/012502, filed on Jan. 22, 2014, all pages.
International Search Report and Written Opinion of PCT/US2014/035798, dated Feb. 11, 2016, all pages.
International Preliminary Report on Patentability dated Feb. 16, 2016 for International Patent Application No. PCT/US2014/035798, filed on Apr. 29, 2014, all pages.
International Search Report and Written Opinion of PCT/US2016/017611, dated May 16, 2016, all pages.
International Search Report and Written Opinion of PCT/US2016/017791, dated May 16, 2016, all pages.
International Search Report and Written Opinion of PCT/US2016/017812, dated Jun. 7, 2016, all pages.
International Search Report and Written Opinion of PCT/US2016/017864, dated Jun. 8, 2016, all pages.
International Search Report and Written Opinion of PCT/US2015/046844, dated Oct. 27, 2015, all pages.
Japanese office action dated Dec. 11, 2015 JP 2013-507344, all pages.
Decision to Grant for JP 2013-507344 dated Jun. 15, 2016, all pages.
Kosaka, et al., "Operating Point Control System for a Continuous Flow Artificial Heart: In Vitro Study," ASAIO Journal 2003, all pages.
Neethu, S., et al., "Novel design, optimization and realization of axial flux motor for implantable blood pump", Power Electronics, Drives and Energy Systems (PEDES) & 2010 Power Indian, 2010 Joint International Conference on, IEEE, Dec. 20, 2010 (Dec. 20, 2010), pp. 1-6.
Sandtner, J., et al., "Electrodynamic Passive Magnetic Bearing with Planar Halbach Arrays", Aug. 6, 2004 (Aug. 6, 2004), retrieved from the internet: <http://www.silphenix.ch/lexington.pdf>, all pages.
Supplementary European Search Report issued in European Application No. 09831788.6, dated Jan. 7, 2013, all pages.
Terumo Heart, Inc., "Handled With Care—Significantly Reduce the Risk of Cell Damage," Terumo brochure, Apr. 2010, 2 pages.
Yamazaki, et al., "Development of a Miniature Intraventricular Axial Flow Blood Pump," ASAIO Journal, 1993, 7 pages.
Extended European Search Report dated May 27, 2019 in European Patent Application No. 16867042.0, filed Nov. 16, 2016, 9 pages.

* cited by examiner

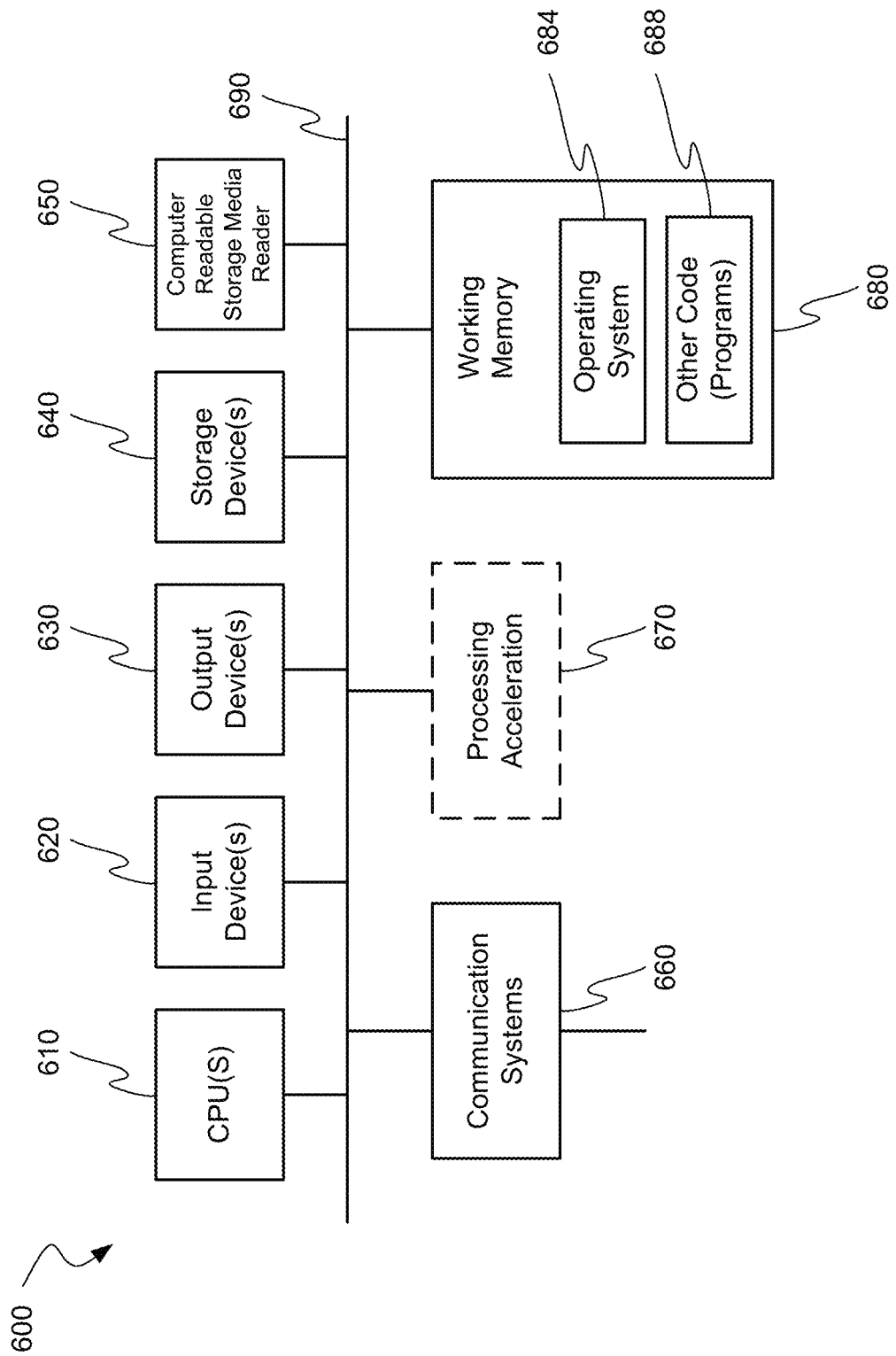

PRESSURE/FLOW CHARACTERISTIC MODIFICATION OF A CENTRIFUGAL PUMP IN A VENTRICULAR ASSIST DEVICE

CROSS REFERENCE TO RELATED APPLICATIONS

This application is a continuation of U.S. patent application Ser. No. 16/173,589, filed Oct. 29, 2018, which is a continuation of U.S. patent application Ser. No. 15/352,141, filed Nov. 15, 2016, now U.S. Pat. No. 10,117,983, issued Nov. 6, 2018, which claims priority to U.S. Provisional Application No. 62/255,774, filed Nov. 16, 2015, which is hereby incorporated by reference in its entirety, for all purposes, as if fully set forth herein.

BACKGROUND OF THE INVENTION

Centrifugal pumps have flatter head pressure-flow (HQ) curve characteristics when compared to axial flow pumps. Due to these flatter HQ curve characteristics, centrifugal pumps provide a lower head pressure as the flow approaches to zero than axial flow pumps when operated in fixed (constant) speed mode. In certain instances, the aortic pressure may momentarily exceed the pump head pressure and result in a low or even retrograde flow through the pump during diastole. A low centrifugal pump flow in diastole may reduce its ventricular unloading capability.

One possible solution is to employ an axial pump instead of the centrifugal pump in the ventricular assist device. FIG. 1 shows the differences between centrifugal and axial pump HQ curves (head pressure versus flow). There are, however, tradeoffs between axial flow and centrifugal flow pumps. For example, some axial flow pumps are associated with increased likelihood of suction events at lower flow conditions and lower maximum pump flow in systole. Additionally, some clinicians may have a preference for a more sensitive pump with a relatively steeper HQ curve.

Yet another possible solution would be to detect systolic and diastolic phases of the cardiac cycle and adjust pump speed accordingly to provide higher pump pressure during low flow conditions, reducing the likelihood of suction events. But this approach requires special sensors and controllers to very reliably detect the characteristics of the cardiac cycle, and may not even work in low pulsatility conditions which may be present in the case of a severely impaired ventricle. Embodiments of the invention provide solutions which overcome these and other problems.

BRIEF DESCRIPTION OF THE INVENTION

In one embodiment, a ventricular assist device is disclosed. The ventricular assist device may include a centrifugal pump and a controller. The controller may be configured to cause the centrifugal pump to operate at a first speed above a predetermined flow rate. The controller may also be configured to cause the centrifugal pump to operate at a second speed below the predetermined flow rate, wherein the predetermined flowrate is indicative of a crossover point between systole and diastole phases of a person's cardiac cycle.

In another embodiment, a method of controlling a centrifugal pump in a ventricular assist device of a person is disclosed. The method may include causing the centrifugal pump to operate at a first speed above a predetermined flow rate. The method may also include causing the centrifugal pump to operate at a second speed below the predetermined flow rate. The predetermined flowrate may be indicative of a crossover point between systole and diastole phases of the person's cardiac cycle.

In another embodiment, a controller for operating a centrifugal pump in a ventricular assist device of a person is disclosed. The controller may include one or more processors. The one or more processors may be configured to execute instructions stored on a non-transitory medium. The instructions may be executable to cause a centrifugal pump to operate at a first speed above a predetermined flow rate. The instructions may also be executable to cause the centrifugal pump to operate at a second speed below the predetermined flow rate. The predetermined flowrate may be indicative of a crossover point between systole and diastole phases of the person's cardiac cycle.

In another embodiment, a non-transitory machine readable medium having instructions stored thereon for operating a centrifugal pump in a ventricular assist device of a person is disclosed. The instructions may be executable by one or more processors to cause a centrifugal pump to operate at a first speed above a predetermined flow rate. The instructions may also be executable to cause the centrifugal pump to operate at a second speed below the predetermined flow rate. The predetermined flowrate may be indicative of a crossover point between systole and diastole phases of a person's cardiac cycle.

BRIEF DESCRIPTION OF THE DRAWINGS

The present invention is described in conjunction with the appended figures:

FIG. 6 is a block diagram of an exemplary computer system capable of being used in at least some portion of the apparatuses or systems of the present invention, or implementing at least some portion of the methods of the present invention.

Figure 1:
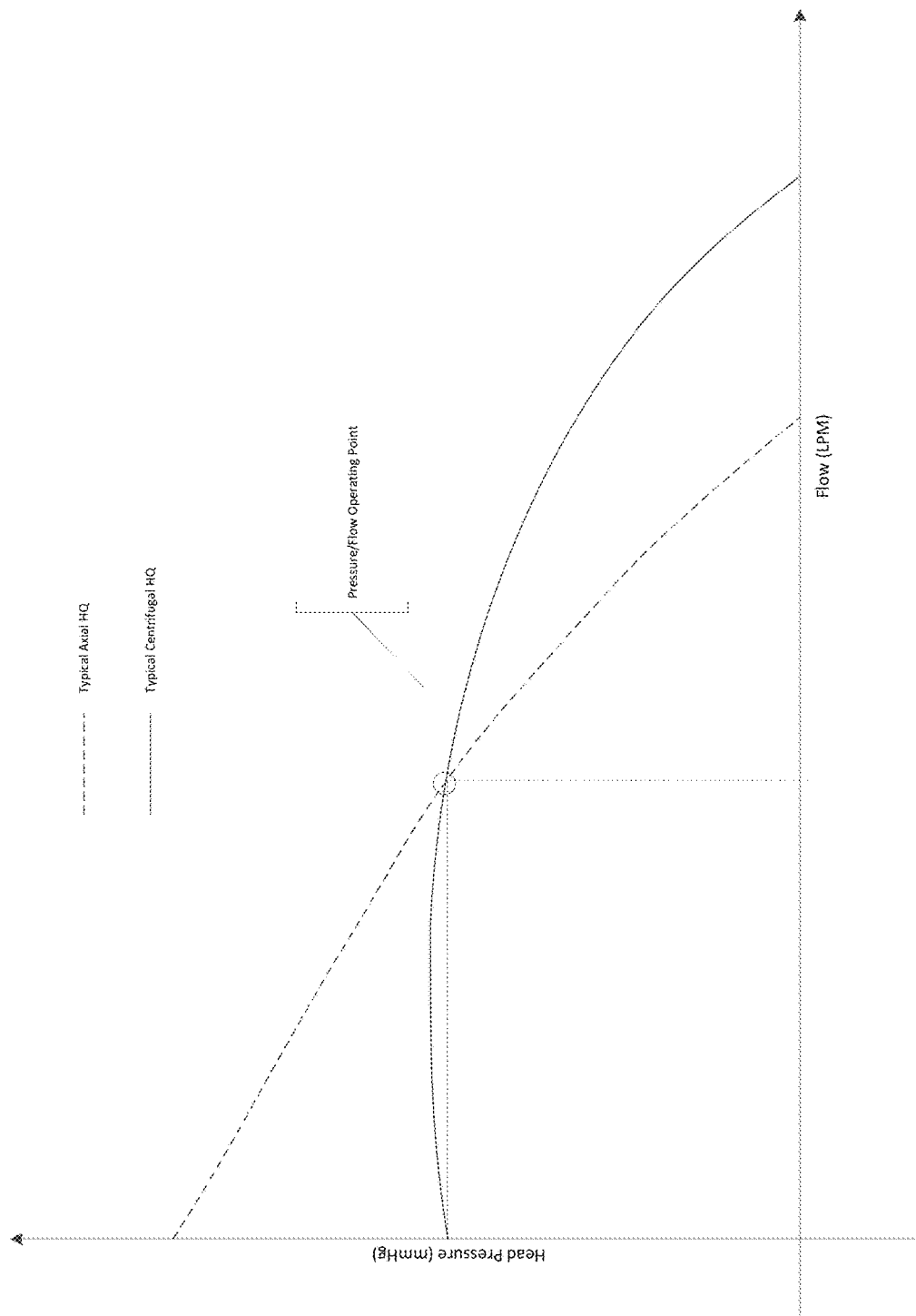
FIG. 1 is a graph showing the head pressure flow curve characteristics (head pressure versus flow) of centrifugal and axial pumps.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

For example, any detail discussed with regard to one embodiment may or may not be present in all contemplated versions of that embodiment. Likewise, any detail discussed with regard to one embodiment may or may not be present in all contemplated versions of other embodiments discussed herein. Finally, the absence of discussion of any detail with regard to embodiment herein shall be an implicit recognition that such detail may or may not be present in any version of any embodiment discussed herein.

Specific details are given in the following description to provide a thorough understanding of the embodiments. However, it will be understood by one of ordinary skill in the art that the embodiments may be practiced without these specific details. For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

The term "machine-readable medium" includes, but is not limited to transitory and non-transitory, portable or fixed storage devices, optical storage devices, wireless channels and various other mediums capable of storing, containing or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

For convenience in explanation and accurate definition in the appended claims, the terms "up" or "upper," "down" or "lower," "inside" and "outside" are used to describe features of the present invention with reference to the positions of such features as displayed in the figures.

Figure 2:
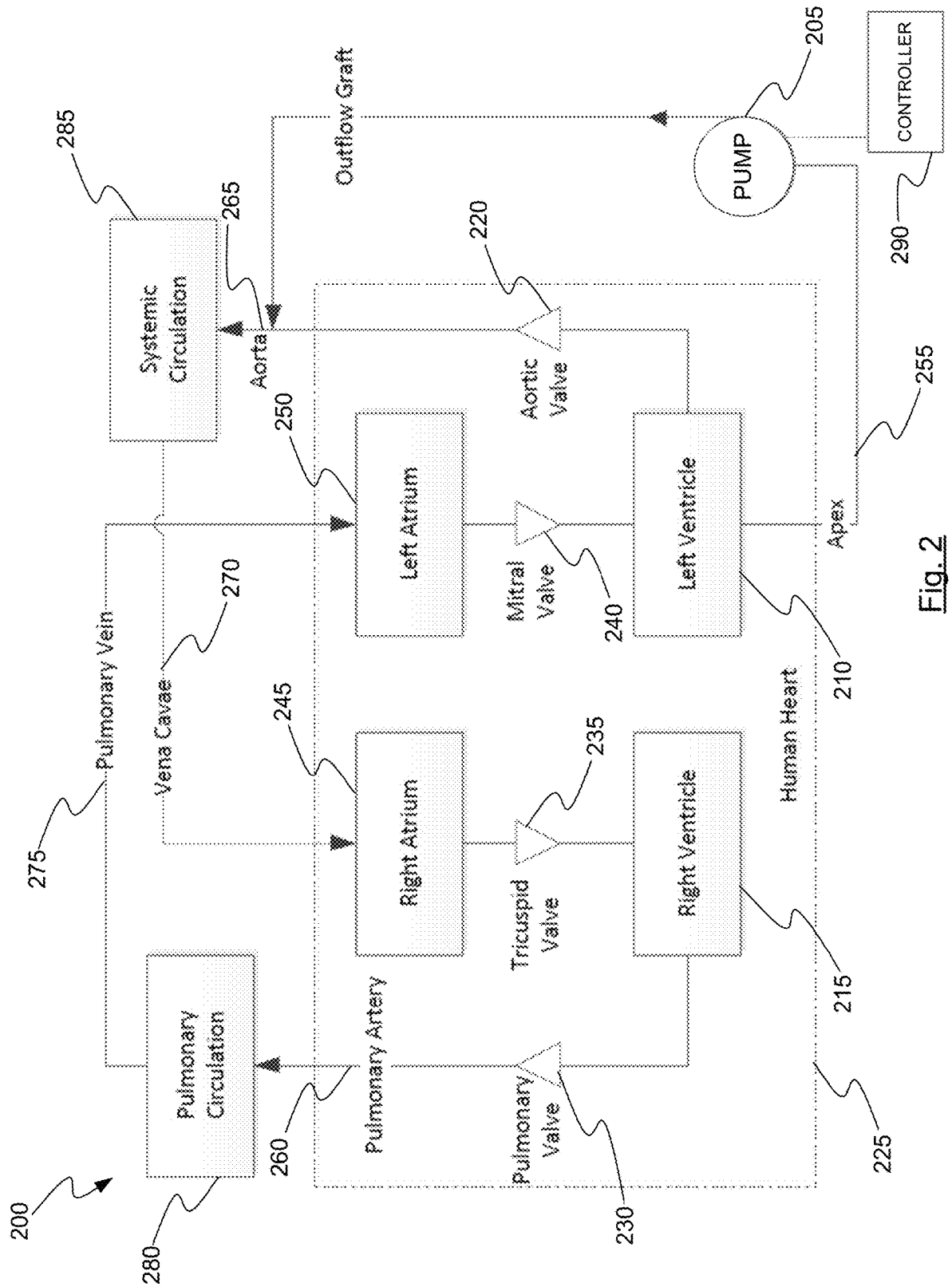
FIG. 2 is a schematic of a system for controlling a blood pump in accordance with embodiments of the present invention.

With reference to FIG. 2 the placement of an exemplary pump 205 in the cardiovascular system will now be described. In various embodiments, the design concept 200 includes pump 205 connected to the left ventricle 210 of a heart 225. Blood is typically drawn into left ventricle 210 from left atrium 250 and expelled to the ascending aorta through aortic valve 220. In the exemplary system, blood from left ventricle 210 is drawn into an inflow of pump 205 and driven through an outflow graft to aorta 265. In the exemplary embodiment, pump 205 is implanted at or near the apex 255 of left ventricle 210. The flow through exemplary pump 205 is estimated using pump parameters which include power/current, speed (RPM) and a flow map, which allows transformation of inputs like power/current and speed to flow based on the pump flow characteristics curves (e.g. HQ head pressure-flow curves). Heart 225 includes pulmonary valve 230, tricuspid valve 235, mitral valve 240, right atrium 245, and left atrium 250. Pulmonary artery 260, aorta 265, vena cavae 270, and pulmonary vein 275 are also shown in FIG. 2. Blocks representing pulmonary circulation 280 and systemic circulation 285 are also shown. A controller 290 may execute operation of pump 205 as will be understood by one of skill in the art from the description herein.

In embodiments of the present invention, pump speed may be controlled such that it operates at a first speed above a predetermined flow rate of blood through the pump, and at a second speed below the predetermined flow rate through the pump. A clinician may set the predetermined flow rate to correspond with a flowrate indicative of a crossover point between the patient's systolic and diastolic cardiac phases. In this manner, the pressure generated by the pump may be increased during the diastolic phase, when pressure generated by the patient's heart on its own is at its lowest. The first speed may represent a minimum operating speed for the pump.

Figure 3:
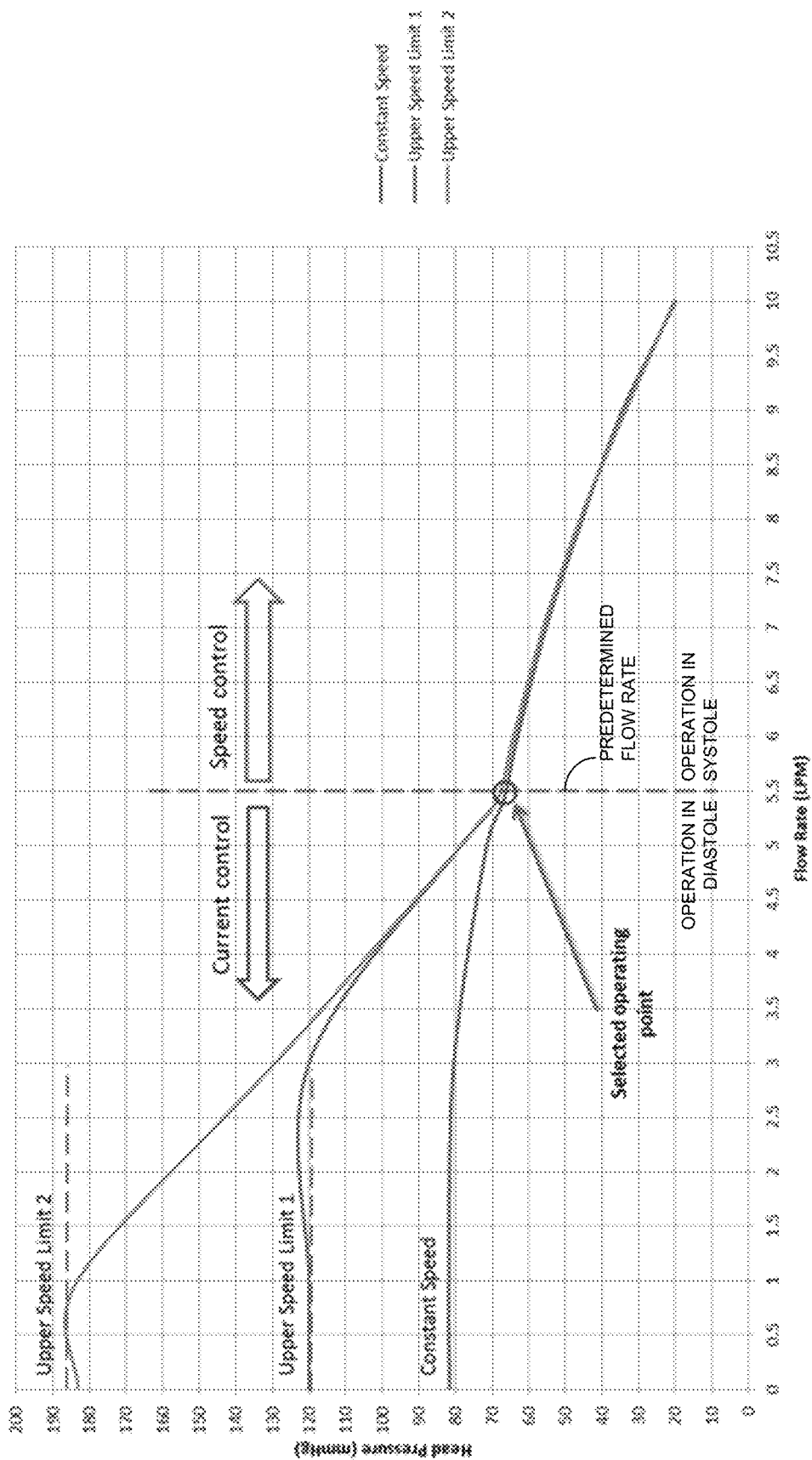
FIG. 3 is a graph showing the head pressure flow curve characteristics (head pressure versus flow) of a centrifugal pump controlled in a manner of one embodiment of the invention.
Figure 4:
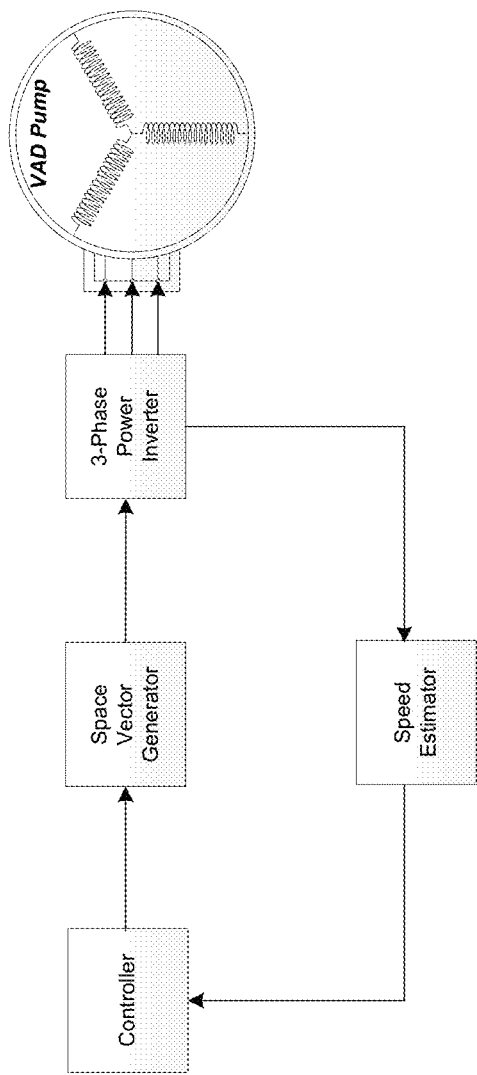
FIG. 4 is a block diagram of one embodiment of the invention for controlling a centrifugal pump to produce the head pressure flow curve shown in FIG. 3.
Figure 5:
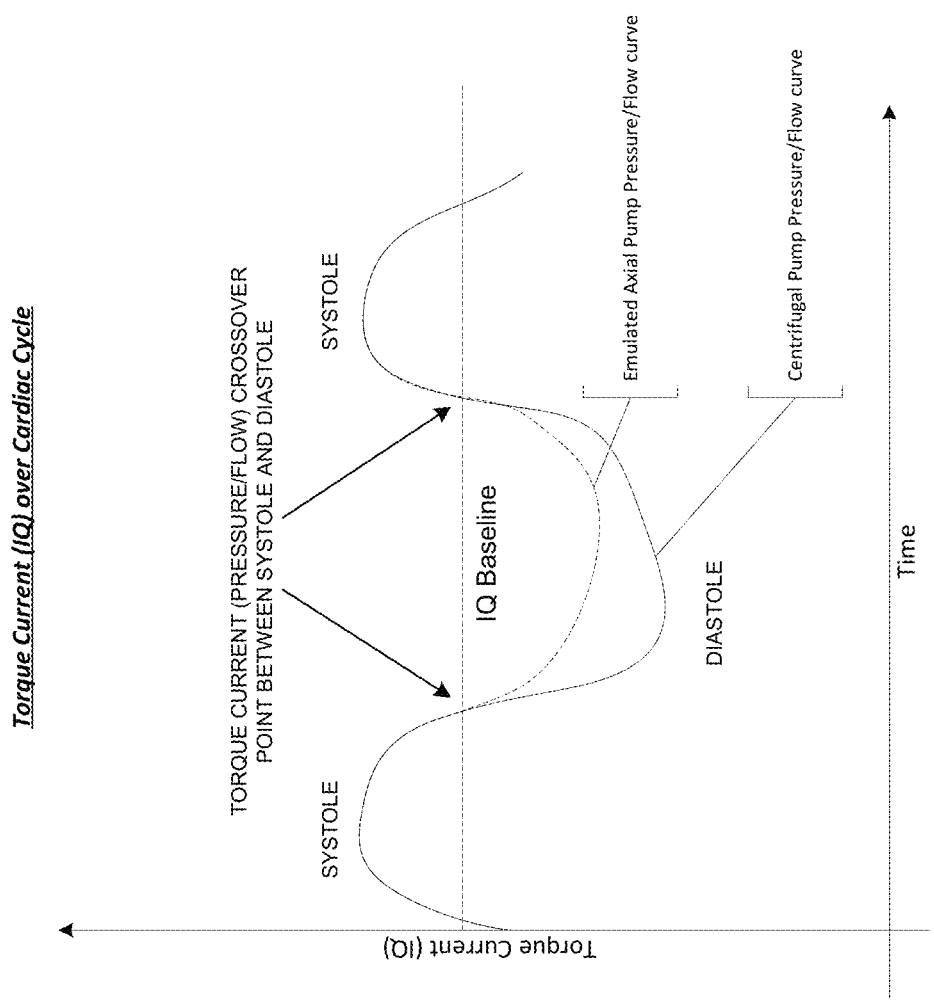
FIG. 5 is a graph showing torque current (IQ) over the cardiac cycle of a patient having a ventricular assist device with a centrifugal pump being operated in two different manners, one according to embodiments of the present invention.

FIG. 3 shows an HQ curve (head pressure versus flow) of a centrifugal pump operated in accordance with such embodiments of the invention using the exemplary system shown in FIG. 4. While the centrifugal pump is operated at a first speed in high flow situations (e.g., in systole), the pump is operated at a higher, second speed, in low flow situations (e.g., in diastole), and thereby simulates the properties of an axial flow pump in low flow situations (e.g., in diastole). Thus, as shown in FIG. 5, by operating a centrifugal pump in this manner, pressure generated may be increased during diastole when compared to operating the centrifugal pump in a conventional manner at a constant set speed across both systole and diastole.

Thus, in one embodiment a method may be provided for controlling a centrifugal pump in a ventricular assist or other device. This method may be conducted by pump controller 290. Pump controller 290 may include a processor and a non-transitory readable medium as discussed further herein.

The method may include causing the centrifugal pump to operate at a first speed above a predetermined flow rate, and causing the centrifugal pump to operate at a second speed below the predetermined flow rate. The first speed may be a minimum set operating speed of the centrifugal pump. The second speed may be greater than the first speed.

When the centrifugal pump is operating at the first speed, a motor of the centrifugal pump may be operating at a variable current but at a constant speed, where the constant speed may be a speed within a certain RPM range, or within 5%, 10%, or other range of the clinician set speed. When the centrifugal pump is operating at the second speed, the motor of the centrifugal pump may be operating at a constant current and/or voltage, so as to maintain a constant back electromotive force (emf), left ventricular pressure, pulmonic pressure, and/or aortic pressure.

To determine when to switch between the first speed and the second speed, the method may include determining an estimated flow rate through the pump based at least in part on a measured current of a motor of the centrifugal pump. The estimated flow rate may then be compared to the predetermined flow rate set by the clinician. In other embodiments, an actual flow rate may be determined with a flow measurement sensor, and then compared to the predetermined flow rate. In some embodiments, the method may also include detecting or identifying a suction event in the centrifugal pump and reducing a speed of the centrifugal pump to alleviate the suction event.

Additional related publications discuss ventricular assist device control schemes and devices which may be applicable to some or all of the disclosed embodiments herein. These publications include U.S. Patent Application Publication Nos. 2014/0323796, 2016/0058930, 2016/0058929, and 2016/0228628 and U.S. Pat. Nos. 7,862,501, 8,096,935, 8,870,552, and 9,039,595. The disclosure of each of the aforementioned patent application publications and patents are hereby incorporated by reference, for all purposes, as if fully set forth herein.

FIG. 6 is a block diagram illustrating an exemplary computer system 600 in which embodiments of the present invention may be implemented. This example illustrates a computer system 600 such as may be used, in whole, in part, or with various modifications, to provide the functions of pump controller 290 and/or other components of the invention such as those discussed above. For example, various functions of pump controller 290 may be controlled by the computer system 600, including, merely by way of example, determining a flow rate through pump 205, causing pump 205 to operate at a constant speed, causing pump 205 to operate at a variable speed, etc.

The computer system 600 is shown comprising hardware elements that may be electrically coupled via a bus 690. The hardware elements may include one or more central processing units 610, one or more input devices 620 (e.g., a mouse, a keyboard, etc.), and one or more output devices 630 (e.g., a display device, a printer, etc.). The computer system 600 may also include one or more storage device 640. By way of example, storage device(s) 640 may be disk drives, optical storage devices, solid-state storage device such as a random access memory ("RAM") and/or a read-only memory ("ROM"), which can be programmable, flash-updateable and/or the like.

The computer system 600 may additionally include a computer-readable storage media reader 650, a communications system 660 (e.g., a modem, a network card (wireless or wired), an infra-red communication device, Bluetooth™ device, cellular communication device, etc.), and working memory 680, which may include RAM and ROM devices as described above. In some embodiments, the computer system 600 may also include a processing acceleration unit 670, which can include a digital signal processor, a special-purpose processor and/or the like.

The computer-readable storage media reader 650 can further be connected to a computer-readable storage medium, together (and, optionally, in combination with storage device(s) 640) comprehensively representing remote, local, fixed, and/or removable storage devices plus storage media for temporarily and/or more permanently containing computer-readable information. The communications system 660 may permit data to be exchanged with a network, system, computer and/or other component described above.

The computer system 600 may also comprise software elements, shown as being currently located within a working memory 680, including an operating system 684 and/or other code 688. It should be appreciated that alternate embodiments of a computer system 600 may have numerous variations from that described above. For example, customized hardware might also be used and/or particular elements might be implemented in hardware, software (including portable software, such as applets), or both. Furthermore, connection to other computing devices such as network input/output and data acquisition devices may also occur.

Software of computer system 600 may include code 688 for implementing any or all of the function of the various elements of the architecture as described herein. For example, software, stored on and/or executed by a computer system such as system 600, can provide the functions of pump controller 290, and/or other components of the invention such as those discussed above. Methods implementable by software on some of these components have been discussed above in more detail. In other embodiments, the methods described herein may be implemented in hardware besides a microprocessor. For example, the methods described herein may be conducted on an application-specific integrated circuit (ASIC) or a field-programmable gate array (FPGA).

The systems and methods described herein provide several advantages over existing approaches. By combining properties of a centrifugal pump in a high flow region (i.e. in systole) and properties of an axial flow pump in a low flow region (i.e. in diastole) the system potentially improves hemodynamics and increases assistance for the failing heart. The present inventions may also improve ventricular unloading and/or the capacity to support patients during exercise and other high capacity periods.

The invention has now been described in detail for the purposes of clarity and understanding. However, it will be appreciated that certain changes and modifications may be practiced within the scope of this disclosure and the appended claims.

What is claimed is:

1. A ventricular assist device, comprising:

a centrifugal pump comprising a motor; and at least one processor configured to:

determine a flow rate through the centrifugal pump based on a current of the motor;

cause the motor to operate at a first speed when the flow rate is greater than a predetermined flow rate during a systolic phase, wherein the predetermined flow rate corresponds with a flow rate indicative of a crossover point between the systolic phase and a diastolic phase, wherein when the motor operates at the first speed, the motor is operating a variable current; and cause the motor to operate at a second speed when the flow rate is less than the predetermined flow rate during the diastolic phase, wherein when the motor operates at the second speed, the motor is operating at one or both of a constant current and a constant speed.

2. The ventricular assist device of claim 1, wherein:
pressure generated by the centrifugal pump is increased during a diastolic phase.

3. The ventricular assist device of claim 1, wherein:
the second speed is greater than the first speed.

4. The ventricular assist device of claim 1, wherein:
the predetermined flowrate is set by a clinician.

5. The ventricular assist device of claim 1, further comprising:
a flow measurement sensor, wherein the flow rate is determined based on a measurement from the flow measurement sensor.

6. The ventricular assist device of claim 1, wherein:
the at least one processor is further configured to:
detect a suction event in the centrifugal pump; and
reduce a speed of the centrifugal pump to alleviate the suction event.

7. A method of controlling a ventricular assist device, comprising:
determining a flow rate through a centrifugal pump of the ventricular assist device based on a current of a motor of the centrifugal pump;
causing a motor of the centrifugal pump to operate at a first speed when the flow rate is greater than a predetermined flow rate during a systolic phase, wherein the predetermined flow rate corresponds with a flow rate indicative of a crossover point between the systolic phase and a diastolic phase, wherein when the motor operates at the first speed, the motor is operating a variable current; and
causing the motor to operate at a second speed when the flow rate is less than the predetermined flow rate during the diastolic phase, wherein when the motor operates at the second speed, the motor is operating at one or both of a constant current and a constant speed.

8. The method of controlling a ventricular assist device of claim 7, wherein:
the first speed is a minimum operating speed of the centrifugal pump.

9. The method of controlling a ventricular assist device of claim 7, wherein:
the first speed is input by a clinician.

10. The method of controlling a ventricular assist device of claim 7, further comprising:
detecting a suction event in the centrifugal pump; and
reducing a speed of the centrifugal pump to alleviate the suction event.

11. The method of controlling a ventricular assist device of claim 7, wherein:
pressure generated by the centrifugal pump is increased during a diastolic phase.

12. A non-transitory machine readable medium having instructions stored thereon, wherein the instructions, when executed, cause at least one processor to perform operations comprising:
determining a flow rate through a centrifugal pump of a ventricular assist device;
causing a motor of the centrifugal pump to operate at a first speed when the flow rate is greater than a predetermined flow rate during a systolic phase, wherein the predetermined flow rate corresponds with a flow rate indicative of a crossover point between the systolic phase and a diastolic phase, wherein when the motor operates at the first speed, the motor is operating a variable current;
causing the motor to operate at a second speed when the flow rate is less than the predetermined flow rate during the diastolic phase, wherein when the motor operates at the second speed, the motor is operating at one or both of a constant current and a constant speed;
detecting a suction event in the centrifugal pump; and
reducing a speed of the centrifugal pump to alleviate the suction event.

13. The non-transitory machine readable medium of claim 12, wherein:
the first speed is within 10% of a clinician set speed.

14. The non-transitory machine readable medium of claim 12, wherein:
the motor maintains one or more of a constant back electromotive force (emf), a constant left ventricular pressure, a constant pulmonic pressure, and a constant aortic pressure.

* * * * *